United States Patent [19]

McIntosh, Sr.

[11] Patent Number: 5,032,310
[45] Date of Patent: Jul. 16, 1991

[54] MICROBIOCIDAL CLEANSING AND DISINFECTING FORMULATIONS AND PREPARATION THEREOF

[75] Inventor: Robert H. McIntosh, Sr., Greensboro, N.C.

[73] Assignee: Interface, Inc., Atlanta, Ga.

[21] Appl. No.: 543,050

[22] Filed: Jun. 22, 1990

Related U.S. Application Data

[63] Continuation-in-part of Ser. No. 80,787, Sep. 3, 1987, abandoned, which is a continuation-in-part of Ser. No. 47,561, Apr. 27, 1987, Pat. No. 4,935,232, and a continuation-in-part of Ser. No. 781,710, Oct. 2, 1985, abandoned, and a continuation-in-part of Ser. No. 635,728, Jul. 30, 1984, abandoned, and a continuation-in-part of Ser. No. 658,695, Oct. 9, 1984, abandoned, and a continuation-in-part of Ser. No. 713,445, Mar. 19, 1985, abandoned, and a continuation-in-part of Ser. No. 736,652, May 21, 1985, Pat. No. 4,647,601, and a continuation-in-part of Ser. No. 744,916, Jun. 13, 1985, abandoned, each is a continuation-in-part of Ser. No. 570,952, Mar. 8, 1984, Pat. No. 4,608,289, which is a continuation of Ser. No. 523,734, Aug. 16, 1983, abandoned, which is a continuation of Ser. No. 226,006, Jan. 19, 1981, abandoned, which is a continuation of Ser. No. 930,879, Aug. 4, 1978, abandoned.

[51] Int. Cl.$^5$ .................... C11D 3/48; A01N 57/00
[52] U.S. Cl. .................... 252/106; 252/174.16; 252/DIG. 14; 514/75; 514/16
[58] Field of Search ............ 252/106, 174.16, DIG. 14

[56] References Cited

U.S. PATENT DOCUMENTS

| | | | |
|---|---|---|---|
| 2,202,134 | 5/1941 | Tattersal | 106/18.17 |
| 2,272,668 | 2/1942 | Honel | 260/403 |
| 2,337,424 | 12/1943 | Stoner et al. | 524/140 |
| 2,541,088 | 2/1951 | Nikawitz | 564/481 |
| 2,552,325 | 5/1951 | Kosolapoff | 558/208 |
| 2,592,564 | 4/1952 | Hardman | 106/284.1 |
| 2,676,122 | 4/1954 | McCarthy | 428/394 |
| 2,756,175 | 7/1956 | Goldstein et al. | 514/187 |
| 2,831,782 | 4/1958 | Zvanut | 72/46 |
| 2,872,351 | 2/1959 | Wedell | 428/270 |
| 2,891,878 | 6/1959 | Chamberlain | 428/421 |
| 2,922,738 | 1/1960 | McDermott et al. | 514/493 |
| 2,934,490 | 5/1960 | Havens et al. | 524/140 |
| 2,936,288 | 5/1960 | Coleman | 252/529 |
| 2,960,529 | 11/1960 | McCall et al. | 558/111 |
| 2,970,081 | 1/1961 | McCall et al. | 424/78 |
| 2,976,186 | 3/1961 | Thompson et al. | 428/393 |
| 2,997,454 | 8/1961 | Leistner et al. | 524/147 |
| 3,247,134 | 4/1966 | Hwa et al. | 521/107 |
| 3,279,986 | 10/1966 | Hyman | 428/245 |
| 3,280,131 | 10/1966 | Wakeman et al. | 546/151 |
| 3,294,775 | 12/1966 | Wasserman | 530/213 |
| 3,308,488 | 3/1967 | Schoonman | 5/500 |
| 3,312,623 | 4/1967 | Fitch et al. | 252/106 |
| 3,364,192 | 1/1968 | Leach | 524/140 |
| 3,404,140 | 10/1968 | Fukumoto et al. | 524/140 |
| 3,428,713 | 2/1969 | Bartlett et al. | 558/208 |
| 3,475,204 | 10/1969 | Patterson | 428/372 |
| 3,498,969 | 3/1970 | Lewis | 536/18.7 |
| 3,527,726 | 9/1970 | Gower et al. | 524/549 |
| 3,577,515 | 5/1971 | Vandegaer | 424/497 |
| 3,620,453 | 11/1971 | Gancberg et al. | 43/131 |
| 3,639,594 | 2/1972 | Notiarianni et al. | 514/76 |

(List continued on next page.)

FOREIGN PATENT DOCUMENTS

| | | |
|---|---|---|
| 1162356 | 2/1984 | Canada . |
| 80101498 | 11/1980 | European Pat. Off. . |
| 0035375 | 9/1981 | European Pat. Off. . |
| 1228031 | 11/1966 | Fed. Rep. of Germany . |
| 2530584 | 1/1977 | Fed. Rep. of Germany . |
| 3014765 | 10/1981 | Fed. Rep. of Germany . |
| 3039437 | 5/1982 | Fed. Rep. of Germany . |
| 3248708 | 7/1984 | Fed. Rep. of Germany . |
| 2237311 | 10/1975 | France . |
| 53-081577 | 7/1978 | Japan . |
| 617854 | 6/1980 | Switzerland . |
| 840218 | 6/1981 | U.S.S.R. . |
| 1122664 | 11/1984 | U.S.S.R. . |
| 1036578 | 7/1966 | United Kingdom . |
| 1302894 | 1/1973 | United Kingdom . |
| 2042574 | 9/1980 | United Kingdom . |
| 2131029 | 6/1984 | United Kingdom . |
| 2157952A | 11/1985 | United Kingdom . |

OTHER PUBLICATIONS

Sorbe et al., *Quim. Apl. Jorn. Com. Esp. Deterg.*, 11th, pp. 415-430 (1980).

Yuan et al., *Phosphorus and Sulphur*, vol. 18, 323-326 (1983).

(List continued on next page.)

*Primary Examiner*—Josephine Barr
*Assistant Examiner*—Cynthia Leslie
*Attorney, Agent, or Firm*—Kilpatrick & Cody

[57] ABSTRACT

A cleansing or disinfecting solution that includes an effective amount of a salt of phosphoric acid or its ester of the formula:

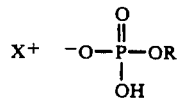

wherein R is selected from the group consisting of hydrogen, methyl, ethyl, propyl, isopropyl, butyl, isobutyl, t-butyl, pentyl, and neopentyl and X is selected from the group consisting of Group IA metals, Group IIA metals, transition metals, and $HNR_1R_2R_3^+$, wherein $R_1$ and $R_2$ are alkyl groups of from 4 to 18 carbon atoms or a hydroxyalkyl group of 1 to 18 carbon atoms, and $R_3$ is an alkyl group of from 8 to 18 carbon atoms, and wherein when R is hydrogen, X is di-(2-hydroxyethyl)-cocoamine. These formulations are effective in killing or inhibiting a wide variety of harmful, destructive or offensive microorganisms including viruses, bacteria, yeasts, algae and molds.

9 Claims, No Drawings

U.S. PATENT DOCUMENTS

| | | | |
|---|---|---|---|
| 3,641,226 | 2/1972 | Partridge et al. | 558/150 |
| 3,671,304 | 6/1972 | Mischutin | 428/254 |
| 3,705,235 | 12/1972 | McIntosh et al. | 424/83 |
| 3,708,573 | 1/1973 | Yoshinaga et al. | 424/489 |
| 3,714,256 | 1/1973 | Samour et al. | 564/288 |
| 3,758,283 | 9/1973 | Matt | 44/366 |
| 3,762,415 | 10/1973 | Morrison | 604/360 |
| 3,769,377 | 10/1973 | De Selms | 558/209 |
| 3,776,806 | 12/1973 | Mayer et al. | 428/289 |
| 3,793,408 | 2/1974 | Schulz | 558/150 |
| 3,819,656 | 6/1974 | Barie, Jr. et al. | 549/316 |
| 3,832,464 | 8/1974 | Hennart | 514/144 |
| 3,873,648 | 3/1975 | Balde | 558/146 |
| 3,885,000 | 5/1975 | Beriger et al. | 558/213 |
| 3,888,978 | 6/1972 | Duwel et al. | 514/76 |
| 3,896,101 | 7/1975 | McIntosh et al. | 524/251 |
| 3,897,491 | 7/1975 | Toy et al. | 562/811 |
| 3,897,521 | 7/1975 | Beriger et al. | 558/183 |
| 3,919,410 | 11/1975 | McIntosh et al. | 424/78 |
| 3,920,836 | 11/1975 | McIntosh et al. | 514/505 |
| 3,925,442 | 12/1975 | Samour | 558/28 |
| 3,928,563 | 12/1975 | McIntosh et al. | 424/78 |
| 3,932,612 | 1/1976 | Burkhardt et al. | 424/78 |
| 3,933,947 | 1/1976 | Kishino et al. | 558/196 |
| 3,959,556 | 5/1976 | Morrison | 428/364 |
| 3,972,243 | 8/1976 | Driscoll et al. | 74/200 |
| 3,979,307 | 9/1976 | Kolaian et al. | 252/8.75 |
| 3,991,187 | 11/1976 | Hogberg et al. | 514/76 |
| 4,004,001 | 1/1977 | Large et al. | 514/80 |
| 4,006,204 | 2/1977 | Rajadhyaksha et al. | 558/210 |
| 4,024,324 | 5/1977 | Sparks | 524/141 |
| 4,025,583 | 5/1977 | Mead et al. | 558/213 |
| 4,039,636 | 8/1977 | Claus et al. | 558/133 |
| 4,071,552 | 1/1978 | Ferland et al. | 562/595 |
| 4,083,860 | 4/1978 | Ruf | 556/13 |
| 4,094,970 | 6/1978 | Behrenz et al. | 424/78 |
| 4,107,292 | 8/1978 | Nemeth | 424/78 |
| 4,110,504 | 8/1978 | Hull et al. | 428/97 |
| 4,119,724 | 10/1978 | Thizy et al. | 424/45 |
| 4,139,616 | 2/1979 | Ducret et al. | 514/141 |
| 4,152,421 | 5/1979 | Tsutsumi et al. | 424/57 |
| 4,209,398 | 6/1980 | Ii et al. | 210/699 |
| 4,235,733 | 11/1980 | Watanabe et al. | 252/107 |
| 4,255,259 | 3/1981 | Hwa et al. | 210/699 |
| 4,259,078 | 3/1981 | Kleber et al. | 8/115.6 |
| 4,272,395 | 6/1981 | Wright | 252/106 |
| 4,276,418 | 6/1981 | Howarth | 544/243 |
| 4,289,634 | 9/1981 | Lewis et al. | 252/32.5 |
| 4,343,853 | 8/1982 | Morrison | 428/233 |
| 4,361,611 | 11/1982 | Schafer et al. | 428/96 |
| 4,363,663 | 12/1982 | Hill | 106/18.31 |
| 4,401,712 | 8/1983 | Morrison | 428/289 |
| 4,432,833 | 2/1984 | Breese | 162/158 |
| 4,442,095 | 4/1984 | Johnston | 514/232.2 |
| 4,442,096 | 4/1984 | Johnston | 514/232.2 |
| 4,560,599 | 12/1985 | Regen | 428/36.1 |
| 4,598,006 | 7/1986 | Sand | 424/81 |
| 4,647,601 | 3/1987 | McIntosh | 514/76 |
| 4,661,477 | 4/1987 | Privitzer et al. | 514/76 |
| 4,770,694 | 9/1988 | Iwasaki et al. | 71/93 |

OTHER PUBLICATIONS

Nakamura, *Journal of Radioanalytical Chemistry*, 52(2), 343–354, (1979).

Nakamura, *Journal of Radioanalytical Chemistry*, 44, 37–47, (1978).

Partridge et al., *J. Inorg. Nucl. Chem.*, 31, 2587–2589, (1969).

Tachimori et al., *Journal of Radioanalytical Chemistry*, 67(2), 329–337, (1981).

Honaker et al., *J. Inorg. Nucl. Chem.*, 39, 1703–1704, (1977).

J. Perka et al., *Tenside Detergents*, 15, 295–298, (1978)6.

Yoshihira Koda et al., "The Synthesis of Surfactant and the use thereof", pp. 96–99 and 436–447, (1977).

Takehiko Fujimoto, "Introduction in New Surfactant", pp. 295–297, (1974).

*J. Inorg. Nucl. Chem.*, 38, 2127–2129, (1976).

Matsui et al., *Chem. Abstracts*, 82, 141561, (1974) (JP 74 24,806).

Ogasawara et al., *Chem. Abstracts* 81, 107078f (1974) (U.S. Pat. No. 3,799,904).

Hall et al., *Chem. Abstracts*, 80, 123000 (1973) ASLE Trans. 16(4), 291–296.

Keil et al., *Chem. Abstracts* 76, 101944k (1972) Ger. Offen. 2,030,256.

Sudakova et al., *Chem. Abstracts*, 76, 56711v (1969) (USSR 229,879).

Gialkdi et al., *Chem. Abstracts* 43, 6363a (1949) (Farm sci. e tec. 4, 166–175).

Tak Chemicals Ltd. 1580026 (Jun. 1977).

McCoy *Microbiology of Cooling Water* 94–95 (Chemical Pub. Co., NY 1980).

Lin Chin-Ann et al., *Surfactant Chemistry*, 85–88 (1978).

Surfactant Science Series, vol. 7, Anionic Surfactant, 504–507 and 545–567 (1976).

Useful Agrochemicals, 408–411.

*Derivatives of Anhydro Acids, 348.*

MICROBIOCIDAL CLEANSING AND DISINFECTING FORMULATIONS AND PREPARATION THEREOF

BACKGROUND OF THE INVENTION

This is a continuation-in-part application of U.S. Ser. No. 080,787, filed Sept. 3, 1987, now abandoned, which is a continuation-in-part of U.S. Ser. No. 047,561, filed on Apr. 27, 1987, now U.S. Pat. No. 4,935,232; 781,710 filed on Oct. 2, 1985, now abandoned; 635,728 filed on July 30, 1984, now abandoned; application Ser. No. 658,695 filed on Oct. 9, 1984, now abandoned; application Ser. No. 713,445 filed on Mar. 19, 1985, now abandoned; application Ser. No. 736,652 filed on May 21, 1985, now U.S. Pat. No. 4,647,601; application Ser. No. 744,916 filed on June 13, 1985, now abandoned; and application Ser. No. 744,730 filed on June 13, 1985, now abandoned; all of which are continuations-in-part of application Ser. No. 570,952 filed Mar. 8, 1984, now U.S. Pat. No. 4,608,289 which in turn was a continuation of application Ser. No. 523,734 filed Aug. 16, 1983, now abandoned, which was a continuation of application Ser. No. 226,006 filed Jan. 19, 1981, now abandoned, which was a continuation of application Ser. No. 930,879 filed Aug. 4, 1978, also now abandoned.

This invention relates microbiocidal cleansing and disinfecting formulations and methods for their preparation and use.

Bacteria, fungi, viruses, algae and other microorganisms are always present in our environment. Such microorganisms are frequently an essential part of ecological systems, industrial processes, and healthy human and animal bodily functions, such as digestion. In other instances, however, microorganisms are highly undesirable because they can cause the illness or death of humans and animals. They can also create odors or damage or destroy a wide variety of materials.

The species and numbers of microorganisms present are dependent on a number of factors, including the availability of nutrients and moisture, the humidity and the temperature of the local environment. Certain bacteria are capable of remaining viable in a dormant state on floors or on objects for long periods of time until they are deposited in the proper media for growth.

Nutrients for microorganisms are typically abundant. For example, dried skin, discarded foods, plants, animal wastes, synthetic and natural materials like plastic coatings and objects, wood, paper, and natural fibers are all excellent nutrient media for many types of microorganisms, including potentially damaging organisms. Microorganisms can degrade useful materials as they feed on them.

A major difficulty in health care facilities, such as hospitals and nursing homes, is the spread of dangerous infectious diseases by microorganisms. The problem is exacerbated in these facilities because many of the patients are in a weakened condition due to illness. A microorganism that would not be a major threat to a healthy person could be fatal to a patient with a diminished capacity to defend himself from infection. Potentially dangerous microorganisms are spread in health care facilities and elsewhere by a variety of means, including on the clothes or skin of health care personnel. The transfer is prevented by cleaning skin or clothes with a nonmicrobiocidal soap or detergent.

Clothing that is used during exercise is particularly susceptible to the accumulation of harmful microorganisms. If these microorganisms are not killed or inhibited, they can cause extensive damage to the fabric, offensive odors and infections. Conventional detergents are often ineffective in killing or removing the microorganisms.

It has proved difficult to develop a microbiocidal cleanser or disinfectant that is effective in controlling the growth of a wide variety of harmful microorganisms and is, at the same time, safe for use around human beings and animals. One of the sources of difficulty in the control of potentially harmful microorganisms is the extreme variability of response of various microorganisms to conventional microbiocidal agents. For example, bacteria, which are classified as procaryotes, can be killed or inhibited by many different types of antibiotics. However, the same antibiotics that are effective against procaryotic organisms are usually ineffective against eucaryotic microorganisms, such as fungi and yeasts.

Even within the family of Bacteriaceae, there are two broad categories of bacteria, Gram-positive and Gram-negative bacteria. These classifications are based on the ability of bacteria to absorb certain vital stains (Gram-negative bacteria absorb positively charged stains and Gram-positive bacteria absorb negatively charged stains). The two groups of bacteria generally also respond differently to the same microbiocidal agent. An antimicrobial agent that is effective against one type of bacteria may not be effective against the other type.

One method of inhibiting the growth of both eucaryotes and procaryotes or both Gram-negative and Gram-positive bacteria is to combine two or more microbiocidal inhibitors that are designed to inhibit or kill a specific organism or class of organisms. However, various problems arise when introducing two or more additives into a material such as a detergent. The multiple additives may alter the physical properties of the detergent. In addition, the multiple components must be tested to insure compatibility and continued microbiocidal effectiveness when combined with the detergent. It is not uncommon for the combination of microbiocidal additives to initially have effective inhibiting or killing properties for both Gram-positive and Gram-negative organisms. However, with the passage of time, one or the other of the inhibiting additives can deteriorate and lose its effectiveness while the other inhibiting additive remains effective. In addition, one additive may have an unexpected inhibitory effect on the other additive. Further, the requirement of adding two or more additives can become prohibitively expensive.

Accordingly, there is a need, both in industry and in the home, for a safe and effective microbiocidal cleanser or disinfectant that can be used on a wide variety of substances.

Therefore, it is an object of the present invention to provide a microbiocidal cleanser or disinfectant that will kill or inhibit a wide variety of microorganisms.

It is another object of the present invention to provide a microbiocidal cleanser or disinfectant that is safe for use around humans and animals.

It is a further object of the present invention to provide a microbiocidal cleanser or disinfectant that can deposit a microbiocidal agent on the object cleaned as a means to impart microbiocidal activity to the object.

SUMMARY OF THE INVENTION

The invention described herein is a microbiocidal cleansing or disinfecting solution, and a method for its preparation, that includes an effective amount of a phosphoric acid ester of the structure

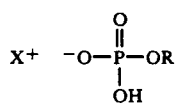

wherein R is selected from the group consisting of hydrogen, methyl, ethyl, propyl, isopropyl, butyl, isobutyl, t-butyl, pentyl, and neopentyl and X is selected from the group consisting of Group IA metals, Group IIA metals, transition metals, and $HNR_1R_2R_3{}^+$, wherein $R_1$ and $R_2$ are alkyl groups of from 4 to 18 carbon atoms or a hydroxyalkyl group of 1 to 18 carbon atoms, and $R_3$ is an alkyl group of from 8 to 18 carbon atoms, and wherein when R is hydrogen, X is di-(2-hydroxyethyl)-cocoamine. These phosphoric acid derivatives are highly water soluble and especially useful in an aqueous disinfectant or detergent.

The microbiocidal cleansing or disinfecting agent can kill or inhibit the growth of many types of bacteria, fungi, viruses, yeasts and other destructive or disease-producing microorganisms that can be found on a surface. The phosphoric acid ester is effective against both Gram-positive bacteria, such as *Staphylococcus aureus*, and Gram-negative bacteria, such as *Pseudomonas aeruginosa*. The phosphoric acid ester is also capable of killing the causative organism of Legionnaires' disease, *Legionella pneumophilia*.

By adjusting the concentration of the reactants in the preparation of the alkyl phosphoric acid ester, bactericidal activity can be selected. For example, the phosphoric acid ester can be prepared so that it is effective primarily against Gram-negative bacteria, against Gram-positive bacteria or both.

The phosphoric acid ester can be added to water to provide a microbiocidal disinfectant solution or can be added to a conventional detergent to provide a microbiocidal cleansing solution. The detergents that can be used in the cleansing solution include, but are not limited to, linear alkyl sulfonates, alkyl benzene sulfonates, and metal salts of long chain fatty acids.

The effective amount of phosphoric acid ester to be used in the cleanser or detergent will vary based on the job to be done. For example, a light duty disinfectant may include from 0.005 to 0.01% (50 to 100 ppm) phosphoric acid ester, whereas a heavy duty cleanser might include from 15 to 70% phosphoric acid ester.

DETAILED DESCRIPTION OF THE INVENTION

As used herein, the term "microorganism" refers to any organism that cannot easily be seen with the naked eye and includes bacteria, molds, yeasts, fungi, algae and viruses. The terms "antimicrobial" and "microbiocidal" describe the killing or inhibition of microorganisms. The term "bactericidal" describes the killing or inhibition of the growth of bacteria. "Fungicidal" describes the killing of, as well as the inhibition of the growth of, fungi, yeasts and molds. The term "viricidal" is used to describe the inactivation or inhibition of viruses. The term "cleansing agent" includes any substance capable of cleaning, emulsifying, or removing unwanted material from a surface. The term "detergent" describes any substance or product which is capable of dislodging, removing, or dispersing solid and liquid soils from a surface being cleansed. The term "detergent" also includes soaps comprising metal salts of long chain fatty acids. The term "disinfectant" includes any liquid that is capable of killing or inhibiting microorganisms.

The present invention is a microbiocidal cleansing or disinfecting solution that includes an effective amount of a phosphoric acid ester of the formula:

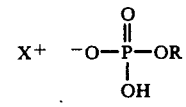

wherein R is selected from the group consisting of hydrogen, methyl, ethyl, propyl, isopropyl, butyl, isobutyl, t-butyl, pentyl, and neopentyl and X is selected from the group consisting of Group IA metals, Group IIA metals, transition metals, and $HNR_1R_2R_3{}^+$, wherein $R_1$ and $R_2$ are alkyl groups of from 4 to 18 carbon atoms or a hydroxyalkyl groups of 1 to 18 carbon atoms, and $R_3$ is an alkyl group of from 8 to 18 carbon atoms, and wherein when R is hydrogen, X is di-(2-hydroxyethyl)-cocoamine. It is believed that at least one free hydroxyl group on the phosphate group is important for substantial microbiocidal activity. In a preferred embodiment, R is ethyl, $R_1$ and $R_2$ are $C_2H_4OH$, and $R_3$ is $C_{12}H_{25}$.

When used as described herein, the solutions are capable of killing or inhibiting the growth of a wide variety of microorganisms including fungi, yeasts, viruses, algae and bacteria. For example, the cleansing or disinfecting solution inhibits the growth of the following representative Gram-negative and Gram-positive bacteria: *Sarcina lutea, Staphylococcus species, Pseudomonas aeruginosa, Pseudomonas cepacia, Escherichia coli, Escherichia communior, Bacillus subtilis, Klebsiella species, Salmonella species, Legionella pneumophilia, Enterobacter aerogenes* and *Streptococcus species*. The cleanser or disinfectant inhibits the growth of the following representative fungi and yeasts: *Candida albicans, Trichophyton metagrophytes, Trichophyton rubrum, Trichophyton interdigitale* and *Aspergillus niger*. The cleanser or disinfectant also inactivates *Herpes simplex* virus. These microorganisms are often present in hospitals and other health care facilities.

The cleanser or disinfectant can be used to impart long term microbiocidal protection to a fiber or fabric. The phosphoric acid ester is mixed with a liquid such as water or other solvent or dispersant and then applied to the fiber by dipping, spraying or washing the fiber or fabric in the solution. When the water or solvent is removed, some of the phosphoric acid ester remains in the fiber or fabric. Thereafter, microorganisms that come into contact with the fiber or fabric will be killed or inhibited. For this application, the concentration of phosphoric acid ester in the water or other solvent or dispersant is preferably between 0.01% and 30% by weight. The preferred concentration of the ester in the dispersant or solvent is between 0.1% and 10% by weight, and most preferred concentration is between 0.5% and 6% by weight. Suitable solvents that can be used to apply the phosphoric acid ester include, but are not limited to, benzene, toluene, xylene, and hexane. Examples of the type of fiber or fabric products contemplated include, but are not limited to, surgical gauze, padding on wound dressings, mattress covers, crib covers, bassinet covers, sailboat sails, tents, draw sheets, cubicle curtains, hair brushes, fabric wall covering, shower curtains, bath mats, athletic clothing, shirts, socks, shorts, pants, shoes and the like, and hospital clothing such as examination robes, physicians coats and nurses uniforms.

The phosphoric acid ester solution can be added to the water in cooling towers to kill or inhibit the growth of the pathogen that causes Legionaire's disease, *Legionella pneumophilia*.

PREPARATION OF PHOSPHORIC ACID ESTER

Monoalkyl phosphoric acid can be produced by reacting $P_2O_5$ with an alcohol, or by any other method known to those skilled in the art. Alternatively, the monoalkyl phosphoric acid ca be purchased commercially.

One mole of $P_2O_5$ reacted with three moles of alcohol produces a mixture predominately of monoalkyl phosphoric acid along with some dialkyl phosphoric acid. In the preferred embodiment, the reaction is carried out at a temperature ranging from 60° to 120° C., and typically at the reflux temperature of the alcohol.

The dialkyl phosphoric acid is a stronger base than the monoalkyl phosphoric acid, and therefore, preferentially reacts with a base added to the product mixture to form a salt. For example, 1.0 m of monoalkyl phosphoric acid and 1.0 m of dialkyl phosphoric acid reacted with 1.3 moles of an amine produces approximately 1.0 m of ammonium dialkyl phosphate, 0.3 m of ammonium monoalkyl phosphoric acid and 0.7 m of monoalkyl phosphoric acid.

In the preferred embodiment, the monoalkyl phosphoric acid is partially neutralized with an organic substituted amine to produce an ammonium salt of an alkyl phosphoric acid.

The alkyl phosphoric acid can instead be partially neutralized with a Group I metal, Group II metal, or transition metal. For example, the alkyl phosphoric acid can be partially neutralized with sodium hydroxide or potassium hydroxide, to produce the sodium or potassium salt of the alkyl phosphoric acid, respectively. Alternatively, the alkyl phosphoric acid can be partially neutralized with magnesium acetate or zinc acetate, to produce the corresponding salts. Since magnesium and zinc are in a +2 oxidation state, each zinc or magnesium ion will coordinate with two molecules of alkyl phosphoric acid.

Selection of the positive ion affects biocidal activity, principally the anti-Gram-negative bactericidal activity, although the alkyl phosphoric acid appears to be the primary source of biocidal activity The biocidal activity is also a function of the relative ratio of mono- to dialkyl substituted phosphoric acid ester.

Without further elaboration, it is believed that one skilled in the art can, using the preceding description, utilize the present invention to the fullest extent. The following specific embodiments, are, therefore, to be construed as merely illustrative, and not limiting of the remainder of the disclosure. Percentage of composition is by weight unless otherwise indicated.

EXAMPLE 1 PREPARATION OF ETHYLPHOSPHORIC ACID

To 3 m of ethanol is slowly added 1 m of $P_2O_5$ with vigorous stirring at a reaction temperature of 60° C. The reaction is complete in about two hours. The progress of reaction is monitored by titrating the acid produced with a solution of base. The reaction products include mono-(ethyl)phosphoric acid and di-(ethyl)phosphoric acid.

EXAMPLE 2 PREPARATION OF THE DI-(2-HYDROXYETHYL)-COCOAMINE SALT OF ETHYLPHOSPHORIC ACID 1.3 Moles of di-(hydroxyethyl)-cocoamine is slowly added to 2.0 moles of the reaction products of Example I (assuming an equal product mixture of mono- and dialkyl phosphoric acid) until the pH is between approximately 2 and 5 (preferably between 3.2 and 3.8) in a 75% ethanol water solution. The reaction is carried out in a temperature range from approximately 60° C. to 120° C. (preferably 100° C.) until the reaction is complete.

The reaction product contains:

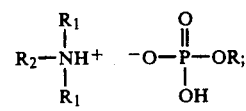

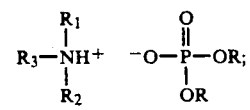

and

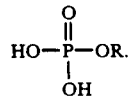

wherein R=ethyl, $R_1$ and $R_2$ are $C_2H_4OH$, and $R_3$ is $C_{12}H_{25}$.

EXAMPLE 3 PREPARATION OF THE ZINC SALT OF ETHYLPHOSPHORIC ACID

The zinc salt of the ethylphosphoric acid mixture is prepared by mixing 32 g of ethylphosphoric acid (as prepared in Example I or purchased commercially) with 15 g of zinc acetate $(Zn(OCO_2CH_3)_2 \cdot 2H_2O)$. These reagents are mixed and then the acetic acid is removed by vacuum distillation.

EXAMPLE 4 PREPARATION OF THE MAGNESIUM SALT OF ETHYLPHOSPHORIC ACID

The magnesium salt of the ethylphosphoric acid mixture is prepared by reacting 20 g of magnesium acetate $(Mg(OCO_2CH_3)_2 \cdot 4H_2O)$ with 32 g of ethylphosphoric acid. The reagents are mixed and warmed, and the acetic acid is then stripped off by vacuum distillation.

MICROBIOCIDAL ACTIVITY OF PHOSPHORIC ACID ESTER

The microbiocidal activity of the phosphoric acid ester or its partially neutralized derivative can be evaluated as follows. Petri dishes are prepared using appropriate nutrient agar as a food source for the microorganism to be tested. The microorganism is seeded into the agar by well known methods. A hole 6 mm in diameter and 5 mm deep is cut into the agar. The test compound (0.05 ml) is placed in the hole and the inoculated petri dish is incubated for 24 hours at 37° C. After the 24 hour incubation period, the relative susceptibility of the test organism to the phosphoric acid derivative is demonstrated by a clear zone of growth inhibition around the test solution. As the phosphoric acid ester diffuses through the agar medium from the hole, its concentration progressively diminishes to a point that it no longer inhibits the test organism. The area of suppressed microbial growth, the zone of inhibition, is a function of the biocidal activity of the compound and its ability to diffuse through the medium.

After the 24 hour incubation period, each plate is examined. The diameters of the complete inhibition zones are measured using reflected light and a measuring device such as a sliding caliper, a ruler, or a template prepared for this purpose and held on the bottom of the plate. The end point, measured to the nearest millimeter, is the point at which no visible growth can be detected with the unaided eye, minus the diameter of the test drop or sample.

EXAMPLE 5 MICROBIOCIDAL ACTIVITY OF MONOALKYL AND DIALKYLPHOSPHORIC ACID

The biocidal activity of three mixtures, 91% mono-(2-ethylhexyl)phosphoric acid and 9% di-(2-ethylhexyl)phosphoric acid ester; 55% mono-(2-ethylhexyl)-phosphoric acid ester and 45% di(2-ethylhexyl)phosphoric acid ester; and 95% di-(2-ethylhexyl) phosphoric acid ester and 5% mono-(2-ethylhexyl)phosphoric acid ester against Gram-positive *Staphylococcus aureus* and Gram-negative *Pseudomonas aeruginosa* were tested using the above-described assay. Each test was performed at least 6 times, and the results averaged. The results are provided in Table 1.

TABLE 1

| Organism | Zone of Inhibition in mm$^2$ | | |
| --- | --- | --- | --- |
| | 91% Mono-ester | Mixture | 95% Di-Ester |
| S. aureus | 352 | 240 | 148 |
| P. aeruginosa | 319 | 148 | 28 |

As shown in Table 1, the monoalkyl phosphoric acid ester has significantly greater activity than the dialkyl phosphoric acid ester against these organisms.

EXAMPLE 6 MICROBIOCIDAL ACTIVITY OF ALKYLPHOSPHORIC ACID NEUTRALIZED WITH VARYING AMOUNTS OF DI(2HYDROXYETHYL)COCOAMINE

Two moles of the product of Example I (using 2-ethylhexyl alcohol in place of ethanol) were neutralized with between 0.5 moles and 3.0 moles of di-(2-hydroxyethyl)cocoamine using the procedure of Example II. The microbiocidal activity of the various mixtures against *S. aureus* and *P. aeruginosa* were then determined using the above-described assay. The results are provided in Table 2.

TABLE 2

| Molar Ratio of reactants | S. aureus Area of Inhibition measured in mm$^2$ | P. aeruginosa |
| --- | --- | --- |
| A. Product from Example I | 3848 | 706 |
| B. 0.5 moles cocoamine$^a$ | 1520 | 614 |
| C. 1.0 moles cocoamine$^a$ | 907 | 706 |
| D. 1.3 moles cocoamine$^a$ | 452 | 1257 |
| E. 1.5 moles cocoamine$^a$ | 452 | 38 |
| F. 2.0 moles cocoamine$^a$ | 452 | 13 |
| G. 2.5 moles cocoamine$^a$ | 201 | 13 |
| H. 3.0 moles cocoamine$^a$ | 153 | 0 |

TABLE 2-continued

| Molar Ratio of reactants | S. aureus Area of Inhibition measured in mm$^2$ | P. aeruginosa |
| --- | --- | --- |
| I. Cocoamine only | 153 | 0 |

$^a$Moles of cocoamine reacted with two moles of the product from Example II.

As shown in Table 2, sample A, which is a mixture of unneutralized mono and dialkylphosphoric acid, has excellent microbiocidal activity against both the Gram positive *Staphylococcus aureus* and the Gram negative *Pseudomonas aeruginosa*. The reaction product from Example I retains its microbiocidal activity against both of these organisms even when reacted with up to 2 moles of di-(2-hydroxyethyl)cocoamine. When two moles of the reaction product from Example I is reacted with more than 2 moles of the cocoamine, the microbiocidal activity is diminished. Although not wanting to be bound to the following mechanism, it is considered that the reduction in microbiocidal activity above 2 moles of the cocoamine is due to the neutralization of the free hydroxyl group of the phosphate group. Three moles of cocoamine neutralize all of the hydroxyl groups in the two moles of reaction product mixture, severely minimizing the microbiocidal activity. As shown, the cocoamine itself has slight microbiocidal activity against the Gram positive *Staphylococcus aureus*.

As illustrated above, the spectrum of activity of the phosphoric acid ester can be manipulated by proper choice of the amount of amine used. For example, the pure, unneutralized phosphoric acid ester is more active against the Gram-positive organism than the Gram-negative organism. The phosphoric acid ester neutralized with 1.3 mole of amine is more active against the Gram-negative organism than the Gram-positive organism.

EXAMPLE 7 MICROBIOCIDAL ACTIVITY OF MAGNESIUM AND ZINC SALTS OF ETHYLPHOSPHORIC ACID

The zinc and magnesium salts of ethylphosphoric acid prepared as described in Examples 3 and 4, respectively, are evaluated for biocidal activity using above-described procedure. Both compounds produce clear zones of inhibition against *S. aureus* and *Pseudomonas aeruginosa*.

EXAMPLE 8 MICROBIOCIAL ACTIVITY OF FABRIC TREATED WITH MICROBIOCIDAL CLEANSER

A microbiocidal cleanser is prepared as described in Example 9. The microbiocidal cleanser is then heated to 85° C. Cotton fabric is added to the cleanser and retained there for a period of 15 minutes. The fabric is then rinsed in water at 40° C., removed, and dried.

Square samples of the treated fabric of approximately 400 mm$^2$ are cut and placed on agar plates which have previously been inoculated with *Staphylococcus aureus* and *Pseudomonas aeruginosa*. The plates are then incubated at 35° C. for 24 hours.

After the incubation, neither *Staphylococcus aureus* nor *Pseudomonas aeruginosa* are found to be present in or on the squares. Microscopic examination shows a zone of inhibition around the individual threads.

PREPARATION OF CLEANSER AND DISINFECTANT

The phosphoric acid ester can be added to water or other solvents to provide a disinfectant formulation or can be added to a conventional detergent to provide a microbiocidal cleansing agent. The detergents that can be used in the present invention include, but are not limited to, linear alkyl sulfonates, alkyl benzene sulfonates, and metal salts of long chain fatty acids.

The phosphoric acid ester is mixed with water or other desired solvent at any desired concentration, preferably between 0.01 and 70% by weight. The effective amount of the phosphoric acid derivative in the cleanser or disinfectant will be determined by its intended use. For example, a solution containing from approximately 0.005 to 0.01% (50 to 100 parts per million (ppm)) of the ester provides an excellent disinfectant formulation for light duty, for example, mopping and cleaning of hard surfaces such as vinyl walls, floors, counters and table tops.

A strong biocidal cleansing formulation such as that required for a surgical scrub, is prepared by mixing the phosphoric acid ester with a conventional detergent at a concentration of between approximately 15% and 70% by weight.

EXAMPLE 9 PREPARATION OF MICROBIOCIDAL CLEANSER

An aqueous microbiocidal cleanser is prepared by mixing 0.05% by weight of the di-(2-hydroxyethyl)-cocoamine salt of ethylphosphoric acid prepared as in Example 2 with an aqueous detergent.

EXAMPLE 10

A microbiocidal cleansing agent can be prepared by (i) neutralizing phosphoric acid with between approximately 1 and 2 moles of di - (2-hydroxyethyl) cocoamine; and (ii) mixing the mixture from step (i) at a concentration of between approximately 0.01% and 70% by weight with a detergent.

EXAMPLE 11 PREPARATION OF MICROBIOCIDAL DISINFECTANT

A disinfectant is prepared by mixing 0.01% by weight of the di-(2-hydroxyethyl)cocoamine salt of ethylphosphoric acid prepared as in Example 2 with water.

EXAMPLE 12 PREPARATION OF DRY FREE FLOWING MICROBIOCIDAL DETERGENT

A dry free-flowing mixture comprising the microbiocidal cleansing agent was prepared by mixing 0.3 grams of the product of Example 2 with 138.5 grams of "All" detergent as purchased over the counter. One gram of the cleansing agent mixture was then placed in the center of inoculated petri dishes and incubated for 24 hours at 37° C. Control plates were also prepared using one gram samples of the detergent without phosphoric acid derivative. After this period of incubation, each plate was examined and the diameters of the inhibition zones were measured. The results are shown in Table 3.

| Organism | Zone of Inhibition in mm² for detergent and alkyl phosphate derivative | Zone of Inhibition in mm² for detergent (Control) |
|---|---|---|
| S. aureus | 2827 | 706 |
| P. aeruginosa | 1017 | 113 |

As shown in Table 3, the detergent along exhibits some microbiocidal activity probably because of the presence of sodium hypochlorite which would be washed out of fabrics during the rinsing process. However, the detergent plus phosphoric acid ester demonstrates a significant increase in microbiocidal activity over the detergent alone.

Modifications and variations of the present invention, microbiocidal cleansing and disinfecting formulations and preparation thereof, will be obvious to those skilled in the art from the foregoing detailed description. Such modifications and variations are intended to come within the scope of the appended claims.

I claim:

1. A microbiocidal cleansing composition comprising a detergent and a biocidally effective amount of a salt of phosphoric acid or its ester of the formula:

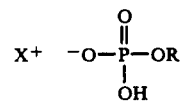

wherein R is selected from the group consisting of hydrogen, methyl, ethyl, propyl, isopropyl, butyl, isobutyl, t-butyl, pentyl, and neopentyl and X is selected from the group consisting of Group IA metals, Group IIA metals, transition metals, and $HNR_1R_2R_3^+$, wherein $R_1$ and $R_2$ are alkyl groups of from 4 to 18 carbon atoms or a hydroxyalkyl groups of 1 to 18 carbon atoms, and $R_3$ is an alkyl group of from 8 to 18 carbon atoms, and wherein when R is hydrogen, X is di-(2-hydroxyethyl)-cocoamine.

2. The microbiocidal cleansing composition of claim 1, wherein $X^+$ is $HNR_1R_2R_3$.

3. The microbiocidal cleansing composition of claim 1, wherein R is ethyl.

4. The microbiocidal cleansing composition of claim 1, wherein X is di-(2-hydroxyethyl)cocoamine and R is hydrogen.

5. A microbiocidal cleansing agent prepared by a process comprising:
   (i) reacting phosphorous pentoxide with 3 moles or more of an alcohol selected from the group consisting of methyl, ethyl, propyl, isopropyl, butyl, isobutyl, t-butyl, pentyl, or neopentyl, per mole of phosphorus pentoxide, at a temperature of between approximately 60° C. and 120° C.;
   (ii) reacting the product of step (i) with between approximately 0.5 to 1.5 moles of a tertiary amine, having one substituent comprising an alkyl group of 8 to 18 carbon atoms, and two substituents being selected from the group consisting of an alkyl group of from 1 to 18 carbon atoms and a hydroxy alkyl group of from 1 to 18 carbon atoms; and then
   (iii) mixing the mixture from step (ii) at a concentration of between approximately 0.01% and 70% by weight with a detergent.

6. The microbiocidal cleansing agent of claim 5, wherein the alchohol is ethyl.

7. The microbiocidal cleansing agent of claim 5, wherein the tertiary amine is di-(2-hydroxyethyl)cocoamine and the alcohol is ethyl.

8. The microbiocidal cleansing agent of claim 5, wherein 1.3 mole of the amine is reacted with the product of step (i).

9. A microbiocidal cleansing agent prepared by
   (i) neutralizing phosphoric acid with between approximately 1 and 2 moles of di-(2-hydroxyethyl) cocoamine; and
   (ii) mixing the mixture from step (i) at a concentration of between approximately 0.01% and 70% by weight with a detergent.

* * * * *